United States Patent [19]

Nappa et al.

[11] Patent Number: 5,395,999

[45] Date of Patent: * Mar. 7, 1995

[54] CATALYTIC CHLOROFLUORINATION PROCESS FOR PRODUCING CHCLFCF$_3$ AND CHF$_2$CF$_3$

[75] Inventors: Mario J. Nappa, Newark; V. N. Mallikarjuna Rao, Wilmington, both of Del.

[73] Assignee: E. I. Du Pont de Nemours and Company, Wilmington, Del.

[ * ] Notice: The portion of the term of this patent subsequent to Nov. 2, 2010 has been disclaimed.

[21] Appl. No.: 139,449

[22] Filed: Oct. 20, 1993

Related U.S. Application Data

[63] Continuation of Ser. No. 972,663, Nov. 6, 1992, abandoned.

[51] Int. Cl.$^6$ .............................................. C07C 17/10
[52] U.S. Cl. ...................................................... 570/169
[58] Field of Search ......................................... 570/169

[56] References Cited

U.S. PATENT DOCUMENTS

| | | |
|---|---|---|
| 3,755,477 | 8/1973 | Firth et al. . |
| 4,129,603 | 12/1978 | Bell . |
| 4,158,675 | 6/1979 | Potter ................................ 570/169 |
| 4,843,181 | 6/1989 | Gumprecht et al. ............... 570/169 |
| 5,036,036 | 7/1991 | Lerou . |
| 5,043,491 | 8/1991 | Webster et al. . |
| 5,057,634 | 10/1991 | Webster et al. . |
| 5,068,472 | 11/1991 | Webster et al. . |
| 5,177,273 | 1/1993 | Bruhnke et al. . |
| 5,258,561 | 11/1993 | Nappa . |

FOREIGN PATENT DOCUMENTS

| | | |
|---|---|---|
| 0313061 | 4/1989 | European Pat. Off. . |
| 0456552 | 11/1991 | European Pat. Off. . |
| 9134612 | 5/1973 | Japan ................................ 570/169 |
| 901297 | 7/1962 | United Kingdom .............. 570/169 |
| 1578933 | 5/1977 | United Kingdom . |
| 2030981 | 8/1978 | United Kingdom . |
| WO90/08755 | 8/1990 | WIPO . |

*Primary Examiner*—Alan Siegel

[57] ABSTRACT

A chlorofluorination process is disclosed which employs a catalyst comprising chromium oxide for producing halohydrocarbons of the formula CHXFCF$_3$ (where X is selected from Cl and F). The process is characterized by feeding a combination of components comprising (i) at least one halohydrocarbon starting compound selected from CHCl=CCl$_2$ and CH$_2$ClCF$_3$, (ii) hydrogen fluoride and (iii) chlorine, to a reaction zone; contacting said combination of compounds in said reaction zone with a catalyst comprising chromium oxide at an elevated temperature to produce reaction zone products containing halohydrocarbons of the formula CHXFCF$_3$ together with halohydrocarbon reaction products of the formula CHYClCF$_3$ (wherein Y is selected from Cl and H); and recovering at least a portion of the reaction zone products from the reaction zone including at least one halohydrocarbon of the formula CHXFCF$_3$. Optionally, a portion of the reaction zone products can be recycled to the reaction zone; and the combination of components contacted with the catalyst can optionally further comprise at least one halohydrocarbon recycle compound of said formula CHYClCF$_3$. The process may be controlled to produce halohydrocarbon compounds of the formula CHXFCF$_3$ in the recovered reaction products as the major component of the halogen-substituted hydrocarbon reaction products in the recovered reaction products.

20 Claims, No Drawings

CATALYTIC CHLOROFLUORINATION PROCESS FOR PRODUCING CHCLFCF$_3$ AND CHF$_2$CF$_3$

This is a continuation of application Ser. No. 07/972,663, filed Nov. 6, 1992, now abandoned.

FIELD OF THE INVENTION

This invention relates to the catalytic chlorofluorination of halogenated ethanes and ethylenes containing chlorine, and more particularly to the production of halogenated ethanes containing fluorine by such chlorofluorination.

BACKGROUND OF THE INVENTION

Many processes have been disclosed for the preparation of 2-chloro-1,1,1,2-tetrafluoroethane (i.e., HCFC-124 or CHClFCF$_3$) and pentafluoroethane (i.e., HFC-125 or CHF$_2$CF$_3$). Typical processes are described in GB 1,578,933 and U.S. Pat. No. 3,755,477. GB 1,578,933 suggests hydrodehalogenation of various halogenated ethanes including 2,2 -dichloro-1,1,1,2-tetrafluoroethane (i.e., CFC-114a or CCl$_2$FCF$_3$) and pentafluoroethane, to form 1,1,1,2-tetrafluoroethane (i.e., HFC-134a or CH$_2$FCF$_3$) and HCFC-124. U.S. Pat. No. 3,755,477 discloses a process for producing fluorinated aliphatic hydrocarbons which comprises fluorinating a halogenated aliphatic hydrocarbon (e.g., 1,1,1-trichloroethane or trichloroethylene) using a gas phase reaction with hydrogen fluoride in the presence of a chromium oxide catalyst. Example 23 therein illustrates using tetrachloroethylene as a raw material, with formation of 20% 2,2-dichloro-1,1,1-trifluoroethane (i.e., CHCl$_2$CF$_3$ or HCFC-123), 20% HCFC-124, 30% HFC-125 and 20% chloropentafluoroethane (i.e., CClF$_2$CF$_3$ or CFC-115).

It is difficult to predict the supply/demand situation for any given hydrofluorocarbon, hydrochlorofluorocarbon or their precursors. There is thus an incentive for developing numerous routes to commercially valuable hydrofluorocarbons and hydrochlorofluorocarbons. HFC-125 and HCFC-124 are useful as refrigerants, blowing agents, fire extinguishants and propellants. Therefore, there is continuing interest in developing efficient methods of producing these materials.

SUMMARY OF THE INVENTION

The present invention provides a process which employs a catalyst comprising chromium oxide for producing halohydrocarbons of the formula CHXFCF$_3$ (where X is selected from Cl and F). The process is characterized by feeding a combination of components comprising (i) at least one halohydrocarbon starting compound selected from CHCl=CCl$_2$ and CH$_2$ClCF$_3$, (ii) hydrogen fluoride and (iii) chlorine, to a reaction zone; contacting said combination of compounds in said reaction zone with a catalyst comprising chromium oxide at an elevated temperature to produce reaction zone products containing halohydrocarbon reaction products of the formula CHXFCF$_3$ together with halohydrocarbons of the formula CHYClCF$_3$ (wherein Y is selected from Cl and H); and recovering at least a portion of the reaction products from the reaction zone including at least one halohydrocarbon of the formula CHXFCF$_3$. Optionally, a portion of the reaction zone products can be recycled to the reaction zone; and the combination of components contacted with the catalyst can optionally further comprise at least one halohydrocarbon recycle compound of the formula CHYClCF$_3$. Advantageous embodiments of the process include providing a contact time and temperature in the reaction zone and an amount of recycle of halohydrocarbons of the formula CHYClCF$_3$ to the reaction zone sufficient to produce halohydrocarbon compounds of the formula CHXFCF$_3$ in the recovered reaction products as the major component of the halogen-substituted hydrocarbon reaction products in the recovered reaction products.

DETAILS OF THE INVENTION

The present invention provides a process for catalytically chlorofluorinating CH$_2$ClCF$_3$ and/or CHCl=CCl$_2$ to produce CF$_3$CHClF and/or CF$_3$CHF$_2$.

In accordance with this invention, CH$_2$ClCF$_3$ and/or CHCl=CCl$_2$, and hydrogen fluoride and chlorine are contacted with a catalyst comprising chromium oxide at elevated temperature to produce CHClFCF$_3$ and CHF$_2$CF$_3$. Preferably, the catalyst consists essentially of chromium oxide. Most preferably the catalyst consists essentially of chromium oxide prepared as described in U.S. Pat. No. 5,036,036, which is hereby incorporated by reference herein in its entirety. This includes catalyst compositions comprising Cr$_2$O$_3$ prepared by pyrolysis of (NH$_4$)$_2$Cr$_2$7 and having an alkali metal content of about 100 ppm or less.

The catalysts of this invention facilitate obtaining high yields of the desired products. Preferably, the compounds CH$_2$ClCF$_3$ and CHCl=CCl$_2$ are converted to provide 2-chloro-1,1,1,2-tetrafluoroethane, pentafluoroethane or in some embodiments, a combination of 2-chloro-1,1,1,2-tetrafluoroethane and pentafluoroethane in total, as the major (i.e., about 50 mole percent or more) chlorofluorination product. Most preferably, the chlorofluorination is run without isomerization of CF$_3$CHClF or disproportionation of CF$_3$CHClF or CF$_3$CHF$_2$.

The chlorofluorination reaction may be conducted in the reaction zone of any suitable reactor, such as a fixed bed reactor. It may be done in a batch or continuous mode; and may be conducted in a single reaction vessel or a combination of reaction vessels. The reaction vessel(s) of the reactor should be constructed of materials which are resistant to the corrosive effects of hydrogen fluoride, hydrogen chloride, and chlorine, such as Hastelloy TM nickel alloy and Inconel TM nickel alloy.

The reaction may be run with or without recycle of at least one halohydrocarbon of the formula CHYClCF$_3$ from the reaction products. Where no recycle is practiced the halohydrocarbon(s) fed to the reaction zone typically consist essentially of CH$_2$ClCF$_3$ and/or CHCl=CCl$_2$. Where recycle is practiced, the halohydrocarbons fed to the reaction zone typically include CHCl$_2$CF$_3$ in addition to CH$_2$ClCF$_3$ (starting material and/or recycle) and/or CHCl=CCl$_2$. Of particular note are embodiments where CHCl=CCl$_2$ starting material and CHYClCF$_3$ recycle (i.e., a saturated recycle) are reacted in a single reaction zone.

The molar ratio of chlorine to the total moles of CHCl=CCl$_2$, CH$_2$ClCF$_3$ and recycled CHCl$_2$CF$_3$ fed to the reaction zone is typically within the range from 0.5:1 to 50:1, and is preferably from 2:1 to 10:1.

The molar ratio of hydrogen fluoride to the total moles of CHCl=CCl$_2$, CH$_2$ClCF$_3$ and recycled CHCl$_2$CF$_3$ fed to the reaction zone is typically within the range of from 2:1 to 100:1, and is preferably from 3:1 to 30:1.

An inert diluent such as argon, helium, or nitrogen may be used in the chlorofluorination reaction of the present invention. If desired, oxygen may be cofed into the reaction zone. The molar ratio of oxygen which may be present during the reaction to the total moles of $CH_2ClCF_3$, $CHCl=CCl_2$ and additional recycle, if any, can vary but will typically be within the range of from 0.001:1 to 1:1. The oxygen may be fed to the reaction zone as such or may be diluted with an inert gas such as nitrogen, helium, or argon. The source of the oxygen may also be air.

The combination of components fed to the reaction zone (i.e., the $CH_2ClCF_3$, $CHCl=CCl_2$, $Cl_2$, HF and other components such as $CHYClCF_3$, oxygen, and/or inert diluents) may be added individually or as mixtures of two or more of the components.

The reaction is conducted at elevated temperature. Generally, the reaction temperature can range from 200° C. to 375° C., and is preferably from about 240° C. to 310° C. The contact time generally will be from about 1 to 60 seconds, and is preferably from about 15 to 30 seconds. Although the chlorofluorination reaction of the present invention is usually conducted at atmospheric pressure, it may also be conducted under elevated or reduced pressure.

2-Chloro-1,1,1,2-tetrafluoroethane and pentafluoroethane in the gaseous mixture discharged from the reactor may be isolated by conventional means, such as distillation. Products of the chlorofluorination reaction of the formula $CHYClCF_3$, where Y is selected from Cl and H, (i.e., $CH_2ClCF_3$ and/or $CHCl_2CF_3$) may be recycled to the chlorofluorination reaction zone to afford additional HCFC-124 and HFC-125.

HF may be present in some embodiment of the invention as an azeotrope or a mixture of azeotropes. Azeotropic compositions containing HF and $CHYClCF_3$ may also be recycled to the reactor.

Practice of the invention will become further apparent from the following non-limiting Examples.

EXAMPLE 1

Chlorofluorination of $CH_2ClCF_3$

A 15 in. (38.1 cm)×⅜ in. (0.95 cm) Hastelloy TM nickel alloy tube was filled with 15.87 g of 12 to 20 mesh (1.7 to 0.84 mm) fresh chrome oxide. The catalyst was activated by heating at 450° C. for 1 hour under a nitrogen purge (50 sccm, $8.3 \times 10^{-7}$ m³/s), then cooled to 300° C. and purged with HF (20 sccm, $3.3 \times 10^{-7}$ m³/s). The flow of HF was then raised to 140 sccm ($2.3 \times 10^{-6}$ m³/s) for one hour. The catalyst bed temperature was reduced to 269° C. and $CH_2ClCF_3$, HF and $Cl_2$ were fed at 1.0 sccm ($1.7 \times 10^{-8}$ m³/s), 40.9 sccm ($6.8 \times 10^{-7}$ m³/s) and 18.4 sccm ($3.1 \times 10^{-7}$ m³/s), respectively. The results of this reaction are shown in Table 1. The bed temperature was then raised to 299° C. and $CH_2ClCF_3$, HF and $Cl_2$ were fed at 0.52 sccm ($8.7 \times 10^{-9}$ m³/s), 58.1 sccm ($9.7 \times 10^{-7}$ m³/s) and 10.8 sccm ($1.8 \times 10^{-7}$ m³/s), respectively. The results of this second reaction are also shown in Table 1.

The reactor effluent was sampled on-line with a Hewlett Packard HP 5880 gas chromatograph using a 20 foot long, ⅛ inch diameter, column containing Krytox TM perfluorinated polyether on an inert support and a helium flow of 35 cc/minute. Gas chromatographic conditions were 70° C. for 3 minutes followed by temperature programming to 180° C. at a rate of 6° C./minute.

TABLE 1

| T(°C.) | %124[a] | %125[b] | %123[c] | %114a[d] | %113[e] | %133a[f] | %114[g] | %115[h] |
|---|---|---|---|---|---|---|---|---|
| 269 | 68 | 9.3 | 7.5 | 5.5 | 3.7 | 3.4 | 2.3 | — |
| 299 | — | 82 | 0.4 | 3.2 | — | 4.1 | 5.1 | 5.0 |

[a]124 = $CHClFCF_3$
[b]125 = $CHF_2CF_3$
[c]123 = $CHCl_2CF_3$
[d]114a = $CCl_2FCF_3$
[e]113 = $CCl_2FCClF_2$
[f]133a = $CH_2ClCF_3$
[g]114 = $CClF_2CClF_2$
[h]115 = $CClF_2CF_3$

HCFC-123 and HCFC-133a, after removal from the product mixture by distillation, may be recycled to the reaction zone to afford additional HCFC-124 and HFC-125.

EXAMPLE 2

Chlorofluorination of $CHCl=CCl_2$

A chrome oxide catalyst was prepared and used in the apparatus described in Example 1 except that 15.09 g of catalyst was used. The catalyst bed was cooled to 275° C. and $CHCl=CCl_2$ (TCE), HF and $Cl_2$ were fed at 3.7 sccm ($6.2 \times 10^{-8}$ m³s), 2.3 sccm ($3.8 \times 10^{-8}$ m³/s) and 28.9 sccm ($4.8 \times 10^{-7}$ m³/s), respectively. The reactor effluent had a molar composition as shown in Table 2.

TABLE 2

| %TCE | %124 | %125 | %123 | %114a | %113 | %133a | %114 | %115 |
|---|---|---|---|---|---|---|---|---|
| 5.3 | 13.1 | 4.8 | 10.1 | 6.5 | 10.1 | 39.6 | 9.7 | 0.8 |

HCFC-123 and HCFC-133a, after removal from the product mixture by distillation, may be recycled to the reaction zone to afford additional HCFC-124 and HFC-125.

Particular embodiments of the invention are illustrated by the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims which follow.

What is claimed is:

1. A process for producing halohydrocarbon compounds of the formula $CHXFCF_3$ wherein X is selected from the group consisting of Cl and F, characterized by:

(a) feeding a combination of components comprising
  (i) at least one halohydrocarbon starting compound selected from $CHCl=CCl_2$ and $CH_2ClCF_3$, (ii) $Cl_2$, (iii) HF and optionally, (iv) at least one halohydrocarbon recycle compound of the formula $CHYClCF_3$ where Y is selected from the group consisting of H and Cl to a reaction zone, wherein the mole ratio of $Cl_2$ to the total moles of $CHCl=CCl_2$, $CH_2ClCF_3$ and recycled $CHCl_2CF_3$ is 0.5:1 or more;
(b) contacting said combination of compounds in said reaction zone with a catalyst comprising chromium oxide at an elevated temperature to produce reaction zone products containing halohydrocarbon reaction products of the formula $CHXFCF_3$ together with halohydrocarbons of the formula $CHYClCF_3$;
(c) recovering at least a portion of the reaction products from the reaction zone including at least one halohydrocarbon of the formula $CHXFCF_3$;
(d) optionally recycling a portion of the reaction zone products to said reaction zone; and
(e) providing a catalyst contact time and temperature in said reaction zone and an amount of recycle of halohydrocarbons of the formula $CHYClCF_3$ to said reaction zone sufficient to produce halohydrocarbon compounds of the formula $CHXFCF_3$ in said recovered reaction products as the major component of the halogen-substituted hydrocarbon reaction products in said recovered reaction products.

2. The process of claim 1 wherein the reaction temperature is within the range of from 200° C. to 375° C.; wherein the molar ratio of $Cl_2$ to the total moles of $CHCl=CCl_2$, $CH_2ClCF_3$, and recycled $CHCl_2CF_3$ is within the range of from 0.5:1 to 50:1; and wherein the molar ratio of HF to the total moles of $CHCl=CCl_2$, $CH_2ClCF_3$, and recycled $CHCl_2CF_3$ is within the range of from 2:1 to 100:1.

3. The process of claim 2 wherein the catalyst consists essentially of chromium oxide.

4. The process of claim 2 wherein the catalyst comprises $Cr_2O_3$ prepared by the pyrolysis of $(NH_4)_2Cr_2O_7$ and having an alkali metal content of about 100 ppm or less.

5. The process of claim 2 wherein the halohydrocarbon starting compound is $CH_2ClCF_3$.

6. The process of any one of claims 2 through 5 wherein $CHF_2CF_3$ is the major component of the halogen-substituted reaction products recovered.

7. The process of claim 2 wherein the halohydrocarbon starting compound is $CHCl=CCl_2$.

8. The process of any one of claims 2, 3, 4, 5, and 7 wherein the process is run with recycle of at least one of said halohydrocarbons of the formula $CHYClCF_3$.

9. A process for producing a halohydrocarbon compound of the formula $CHF_2CF_3$ characterized by:
  (a) feeding a combination of components comprising
    (i) at least one halohydrocarbon starting compound selected from $CHCl=CCl_2$, (ii) $Cl_2$, (iii) HF and optionally, (iv) at least one halohydrocarbon recycle compound of the formula $CHYClCF_3$ where Y is selected from the group consisting of H and Cl to the reaction zone, wherein the molar ratio of $Cl_2$ to the total moles of $CHCl=CCl_2$, $CH_2ClCF_3$ and recycled $CHCl_2CF_3$ is within the range of from 0.5:1 to 50:1;
  (b) contacting said combination of compounds in said reaction zone with a catalyst comprising chromium oxide at an elevated temperature to produce reaction zone products containing halohydrocarbon reaction products including $CHF_2CF_3$ together with halohydrocarbons of the formula $CHYClCF_3$;
  (c) recovering at least a portion of the reaction products from the reaction zone including $CHF_2CF_3$;
  (d) optionally recycling a portion of the reaction zone products to said reaction zone; and
  (e) providing a catalyst contact time and temperature in said reaction zone and an amount of recycle of halohydrocarbons of the formula $CHYClCF_3$ to said reaction zone sufficient to produce $CHF_2CF_3$ in said recovered reaction products as the major component of the halogen-substituted hydrocarbon reaction products in said recovered reaction products.

10. The process of claim 9 wherein the catalyst consisting essentially of chromium oxide; and wherein the process is run with recycle of at least one of said halohydrocarbons of the formula $CHYClCF_3$.

11. The process of claim 10 wherein the reaction temperature is within the range of from 200° C. to 375° C.; wherein the molar ratio of $Cl_2$ to the total moles of $CHCl=CCl_2$, $CH_2ClCF_3$, and recycled $CHCl_2CF_3$ is within the range of from 2:1 to 50:1; and wherein the molar ratio of HF to the total moles of $CHCl=CCl_2$, $CH_2ClCF_3$, and recycled $CHCl_2CF_3$ is within the range of from 2:1 to 100:1.

12. A process for producing a halohydrocarbon compound of the formula $CHF_2CF_3$, characterized by:
  (a) feeding a combination of components comprising
    (i) at least one halohydrocarbon starting compound selected from $CHCl=CCl_2$ and $CH_2ClCF_3$, (ii) $Cl_2$, (iii) HF and (iv) at least one halohydrocarbon recycle compound of the formula $CHYClCF_3$ where Y is selected from the group consisting of H and Cl to a reaction zone, wherein the molar ratio of $Cl_2$ to the total moles of $CHCl=CCl_2$, $CH_2ClCF_3$ and recycled $CHCl_2CF_3$ is within the range of 0.5:1 to 50:1;
  (b) contacting said combination of compounds in said reaction zone with a catalyst composition comprising a catalytically effective amount of chromium oxide or HF-activated chromium oxide at a temperature of at least about 200° C. to produce reaction zone products containing halohydrocarbon reaction products including $CHF_2CF_3$ together with halohydrocarbons of the formula $CHYClCF_3$;
  (c) recovering at least a portion of the reaction products from the reaction zone including $CHF_2CF_3$;
  (d) recycling a portion of the reaction zone products including at least one compound of the formula $CHYClCF_3$ to said reaction zone; and
  (e) providing a catalyst contact time and temperature in said reaction zone and an amount of recycle of halohydrocarbons of the formula $CHYClCF_3$ to said reaction zone sufficient to produce $CHF_2CF_3$ in said recovered reaction products as the major component of the halogen-substituted hydrocarbon reaction products in said recovered reaction products.

13. The process of claim 12 wherein the reaction temperature is within the range of from 200° C. to 375° C.; wherein the molar ratio of $Cl_2$ to the total moles of $CHCl=CCl_2$, $CH_2ClCF_3$, and recycled $CHCl_2CF_3$ is within the range of from 2:1 to 50:1; and wherein the molar ratio of HF to the total moles of $CHCl=CCl_2$, $CH_2ClCF_3$, and recycled $CHCl_2CF_3$ is within the range of from 2:1 to 100:1.

14. The process of claim 1 wherein an inert diluent is present during catalyst contact.

15. The process of claim 1 wherein the combination of components fed to the reaction zone further comprises oxygen.

16. The process of claim 15 wherein the molar ratio of oxygen to the total moles of $CH_2ClCF_3$, $CHCl=CCl_2$ and recycle compound of the formula $CHYClCF_3$ present, is within the range of from 0.001:1 to 1:1.

17. The process of claim 15 wherein an inert diluent is present during catalyst contact.

18. The process of claim 15 wherein the source of oxygen is air.

19. The process of claim 1 wherein HF is present as an azeotrope or a mixture of azeotropes.

20. The process of claim 1 wherein an azeotropic composition containing HF and $CHYClCF_3$ are recycled to the reaction zone.

* * * * *